(12) United States Patent
Wu et al.

(10) Patent No.: US 9,581,533 B2
(45) Date of Patent: Feb. 28, 2017

(54) MODULAR HARDNESS TESTING MACHINE

(71) Applicants: Shaoming Wu, Thousand Oaks, CA (US); Richard Wu, Thousand Oaks, CA (US)

(72) Inventors: Shaoming Wu, Thousand Oaks, CA (US); Richard Wu, Thousand Oaks, CA (US)

( * ) Notice: Subject to any disclaimer, the term of this patent is extended or adjusted under 35 U.S.C. 154(b) by 378 days.

(21) Appl. No.: 14/246,492

(22) Filed: Apr. 7, 2014

(65) Prior Publication Data

US 2015/0285722 A1    Oct. 8, 2015

(51) Int. Cl.
*G01N 3/42* (2006.01)

(52) U.S. Cl.
CPC ......... *G01N 3/42* (2013.01); *G01N 2203/0078* (2013.01); *G01N 2203/0206* (2013.01)

(58) Field of Classification Search
USPC ................................................. 73/81, 82, 83
See application file for complete search history.

(56) References Cited

U.S. PATENT DOCUMENTS

| 4,435,976 A * | 3/1984 | Edward, Jr. | G01N 3/44 73/83 |
| 5,616,857 A * | 4/1997 | Merck, Jr. | G01N 3/42 73/82 |
| 6,247,356 B1 * | 6/2001 | Merck, Jr. | G01N 3/42 73/82 |
| 7,066,013 B2 * | 6/2006 | Wu | G01N 3/42 73/82 |
| 2003/0196480 A1 * | 10/2003 | Anderberg | G01N 3/48 73/81 |
| 2011/0132078 A1 * | 6/2011 | Wu | G01N 3/08 73/81 |

* cited by examiner

*Primary Examiner* — Paul West
*Assistant Examiner* — Mark A Shabman
(74) *Attorney, Agent, or Firm* — Clement Cheng

(57) ABSTRACT

A modular hardness testing machine has a measuring component and a set of frames. The measuring component includes a housing and locating slot. The measuring component has a locating slot configured to receive a frame. The locating slot allows a user to modularly interchange the frame. The measuring component's housing encloses a presshead, which encloses a load cell having through-holes holding transmission pins. The first end of each transmission pin contacts a displacement measurement sleeve, and a second end contacts a transmission plate. A motor is mounted to the housing. The motor is connected to a reduction drive. The reduction drive reduces speed and drives a lead screw mounted on a bearing mount, and a moveable presshead is driven by the lead screw.

17 Claims, 6 Drawing Sheets

MODULAR HARDNESS TESTING MACHINE

FIELD OF INVENTION

The present invention relates to a material hardness measuring device, and more specifically to a penetration hardness tester, which allows the user to measure, to high precision, the hardness of materials, using many types of hardness tests.

DISCUSSION OF RELATED ART

Well-known to those in the field, in order to ensure product quality, manufacturers and laboratories need to measure and control hardness of products. In this respect, NIST (National Institute of Standards and Technology) and ASTM (American Society for Testing and Materials) issued standards for metallic material hardness, standards for hardness test block traceability and standards for hardness testers.

For example, a traditional Rockwell hardness tester includes a measuring component base, which fixes an indenter, dial indicator, and a lever, and a deadweight hung on the lever. Via the lever, the force of the deadweight is transferred to the indenter, causing the indenter to indent into test specimens. Then, the dial indicator measures the depth of indentation, and then calculates the hardness according to the depth.

A Rockwell test requires a 150 kg force. Using a 150 kg deadweight is too heavy for a laboratory machine, so designers use a 15 kg deadweight and amplify the applied force to 150 kg force through levers. Because these mechanical parts wear down over time, the force will eventually become inaccurate. After the indenter penetrates to some depth in the test specimen, a measurement is made of the depth. Prior art penetration hardness testers have moving mechanical parts moving relative to each other. Such relative mechanical movement can contribute to sources of friction or lost (non-recoverable) displacement between the point of displacement measurement and the test specimens so as to impair the repeated accuracy of the hardness test.

The use of deadweight testers and their mechanical impreciseness over time has led to the use of feedback control closed loop systems employing a load cell as part of the means to measure the application of force to the test specimen.

U.S. Pat. No. 4,435,976 describes the use of a load cell to determine the forces applied during Brinell tests and employs a feedback loop to automatically compensate for factors which affect the accuracy of the measurements, such factors being temperature and friction.

Another instance U.S. Pat. No. 6,142,010 describes the use of control closed loop systems including a load cell to measure and apply force for a Rockwell tester.

Another instance U.S. Pat. No. 6,247,356 describes the use of control closed loop systems including a load cell to measure and apply force for a micro hardness tester.

Another instance U.S. Pat. No. 8,132,447 describes a Universal Testing Machine. This test machine utilizes a measuring component base which can be fitted with different measurement devices to measure with different hardness test methods.

The above hardness testers can only apply a vertical force, which is suitable for laboratory testing, but insufficient for workshop testing, which may test complex-shaped test specimens in complicated test environments.

Another instance U.S. Pat. No. 7,066,013 describes a portable hardness tester. The implementation of this patent gives inaccurate test results because the load cell and displacement sensor are installed in incorrect places which adds nonlinearity. Another limitation is the force is supplied by hand, which is inaccurate.

SUMMARY OF THE INVENTION

Accordingly, it is an object of this invention to provide a new concept testing machine which performs multiple types of indentation hardness testing: Rockwell, Superficial Rockwell, Brinell, Vickers, Micro Vickers and Knoop, and so on.

The tester in the present invention is conceptually different from previous testers in that it is more suitable for workshops. This kind of tester can meet all needs of workshops which must test complex-shaped test specimens and in complicated test environments. This tester can apply force in any direction for measurement of test specimens.

An object of the present invention is to provide an apparatus with easy operation and highly accurate measurements. The apparatus is capable of automatically and efficiently performing measurements.

Another object of the invention is to provide a testing machine with a simpler structure, to lower costs and require less maintenance.

The present invention is conceptually different from previous testers in that instead of a single device like in prior testers, the inventive testing machine comprises a module, which comprises a measuring component and a set of frames, such as a column style stand and retaining frames. The metallic measuring component includes a housing and locating slot; the housing is perpendicular to the locating slot. The locating slot is for affixing all types of frames.

Another object of the invention is to provide a testing machine with a measuring component. The present invention's measuring apparatus's metallic measuring component includes a housing which fixes in place the motor, reduction drive, the lead screw, and a moveable presshead. The rear of the presshead fixes a nut. The motor is connected to the reduction drive, which reduces speed and drives the lead screw. The nut converts the rotary motion of the lead screw into linear motion. The presshead can freely move in the cavity at the front of the housing. The measuring component also includes a circuit housing for the electronics systems.

Another object of the invention is to provide a testing machine with a measuring component. The present invention's measuring apparatus's measuring component's presshead comprises an assembly of components. The assembly includes a presshead housing, force sensor, displacement sensor, nut, displacement measurement sleeve, guide sleeve, and indenter.

Another object of the invention is to provide a testing machine with a measuring component. The present invention's measuring apparatus's measuring component's force sensor is a strain gage type load cell. The measuring component's displacement sensor is a capacitive type sensor, optical grating sensor, or Linear Variable Differential Transformer sensor. The displacement sensor directly measures the indentation depth on the surface of the specimen formed by the indenter. This removes displacement errors from transfer displacements and results in high accuracy measurements.

Another object of the invention is to provide a testing machine with a measuring component. The present invention's measuring apparatus's measuring component's electronics system comprises a motion control and driver system, data processing system, data display system, and data communication system. The motion control and driver system is a closed-loop digital control system, which generates accurate force to the indenter. Also, this system driver moves the presshead quickly forward or backward. The data processing system calculates and analyzes the hardness according to indentation depth on the test specimen produced by the indenter. The LCD of the data display system displays test results. The data communication system transfers test results to a PC or printer through an USB or Bluetooth™ interface.

Another object of the invention is to provide a testing machine with a measuring component. The present invention's measuring apparatus's measuring component's power supply system is a rechargeable battery for user convenience.

Another object of the invention is to provide a testing machine with a measuring component. The present invention's measuring apparatus's measuring component's presshead can switch between different indenters dependent on test scales.

Another object of the invention is to provide a testing machine with a set of different frames. Users select different frames suitable for different test specimens such as long specimens, short specimens, holes or thin-walled tubes.

Another object of the invention is to provide a testing machine with a set of different frames. One of these frames is a column style stand which forms the testing apparatus. The stand comprises a box frame which has equally spaced slots. The measuring component connects to the stand by a fastening fixture. Repositioning the fastening fixture on the box frame makes large adjustments in the height between the test specimen and indenter. The column style stand not only can stand in vertical position, but also in horizontal or any direction position. This satisfies many users' testing requirements. Traditional hardness testers instead employ a long screw system for adjusting the height between the test specimen and indenter, so their dimensions are too big and can stand only in a vertical position, limiting users' testing options.

According to the present invention, the foregoing and other objects and advantages are attained by providing a testing machine, comprising:

A module for performing various hardness tests that specialize in indentation hardness testing. The module comprises a measuring component and a set of frames. The user selects the frame according with the test specimen and with the measuring component easily composes the hardness testing machine. The measuring component comprises the load cell, the displacement sensor, motion control and driver system, data processing system, data display system, and data communication system. The motion control and driver system is a closed-loop digital control system, which generates accurate force to the indenter. The data processing system calculates and analyzes the hardness according to the indentation on the test specimen produced by the indenter. The LCD in the data display system displays test results. The data communication system transfers test results to a PC or printer through an USB or Bluetooth™ interface.

In accordance with another aspect of the invention, the present invention provides a method of testing a test specimen via a testing machine, comprising the steps of:

(a) In order to perform one of several available hardness tests on the test specimen, the user selects one of many different frames and a measuring component, which together compose a specialized hardness test machine.

(b) The user places test specimen between the indenter and anvil, and starts the test machine.

(c) The motion control and driver system turns on the motor and moves the presshead, which applies a force onto the indenter, which produces an indentation on the test specimen following NIST's standard's testing procedure.

(d) The data display system shows test results.

(e) The data communication system transfers the test results to a PC or printer through USB or Bluetooth™.

Still further objects and advantages will become apparent from a consideration of the ensuing description and drawings.

These and other objectives, features, and advantages of the present invention will become apparent from the following detailed description, the accompanying drawings, and the appended claims.

The following callouts of elements can be a useful guide in referencing the elements of the drawings.

10 Measuring Component
20 Column Style Stand
30 Test Specimen
100 Housing
101 Presshead
102 Motor
103 Reduction Drive
104 Bearing Mount
105 Lead Screw
106 Circuit Housing
201 Box Frame
202 Fastening Fixture
203 Screw
204 Anvil
205 Nut
206 Base 400 Retaining Frame
401 Retaining Frame Cavity
402 Positioning Key
403 Self-Aligning Anvil
404 Half Ball
405 Anvil
500 Thin-Walled Tube Testing Frame
501 Cylinder
502 L-Shaped Frame
503 Positioning Key
114 Locating Slot
51 Presshead Housing Shell
52 Force Sensor Load Cell
53 Displacement Sensor
54 Nut
55 Displacement Measurement Sleeve
56 Indenter
57 Guide Sleeve
58 Spring
59 Set Screw
61 Set Screw Tip
62 Transmission Pins
63 Transmission Plate
64 Sensor Axle
65 Round Steel Leaves
66 Fixed Electrical Terminals
67 Moveable Electrical Terminal
68 Spring Pad
69 Spring
49 Capacitance Conditioning Circuit
41 Protrusion
42 Gap
43 Circumferential Groove
44 Front Surface
45 Indenter Front End
46 Indenter Protrusion
47 Indenter Rear End
48 Equally Spaced Slots

DETAILED DESCRIPTION OF THE PREFERRED EMBODIMENT

Figure 1:
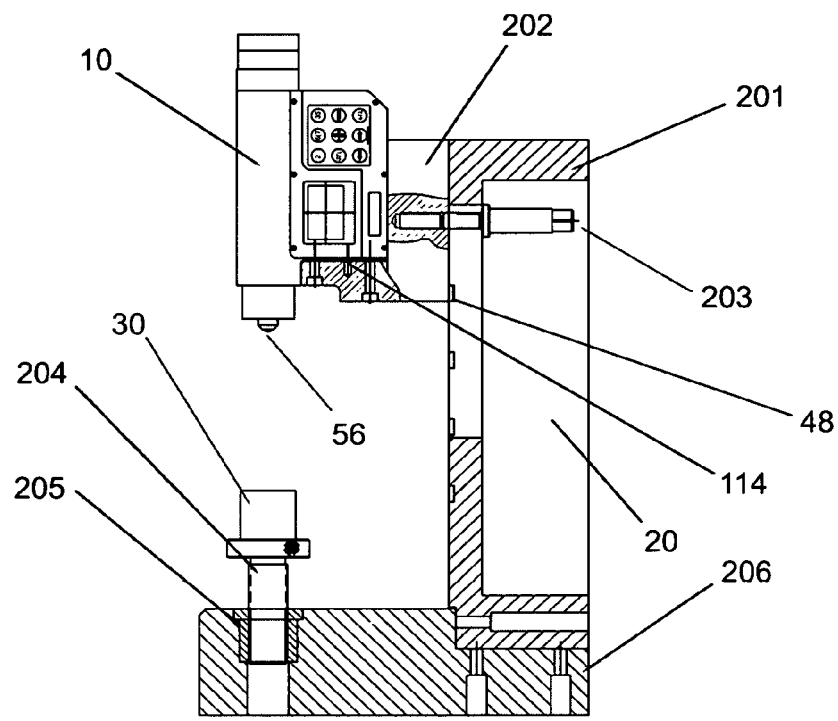
FIG. 1 is a view of the testing machine with column style stand according to the preferred embodiment of the present invention.
Figure 11:
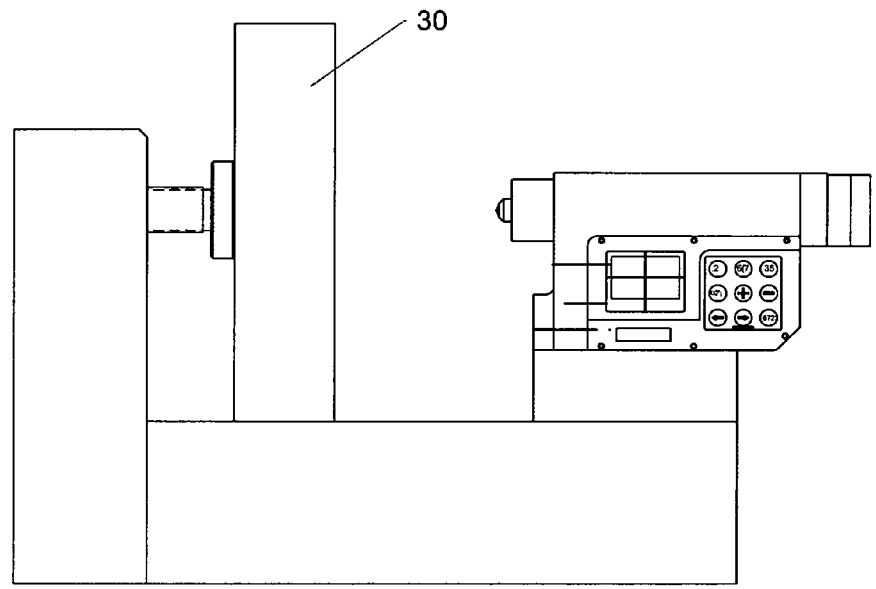
FIG. 11 is a view of the testing machine with column style stand placed horizontally according to the above preferred embodiment of the present invention.

Description will now be given of the inventive testing machine with reference to FIG. 1. As shown in FIG. 1, the testing machine comprises a first module and a second module that can modularly attach to each other and detach from each other with or without tools. The testing machine first module has a measuring component that is configured to attach to the second module which is one frame that is selected from a set of frames. FIG. 1 shows the measuring component 10 and a column style stand 20 which forms the testing apparatus. The stand 20 comprises a box frame 201, which is fixed to a fastening fixture 202, screw 203, anvil 204, nut 205, and base 206. A fastening fixture 202 connects the measuring component 10 to the stand 20. The box frame 201 has equally spaced slots 48. The fastening fixture 202 has a positioning key, which inserts into one of the slots 48. The fastening fixture 202 can be inserted into any of the slots 48 on the box frame 201 and fastened onto said box frame 201 with a screw 203. The anvil 204 is used for supporting test specimens 30, and is attached to base 206 by a nut 205. One end of the anvil is a screw, which screws into the nut 205. The anvil 204 is also used to make small adjustments in the height between the test specimen 30 and indenter 56. Repositioning the fastening fixture 202 on the box frame 201 makes large adjustments in the height between the test specimen 30 and indenter 56. The column style stand can stand in not only a vertical position, but also a horizontal or any direction position. FIG. 11 shows the column style stand placed in a horizontal position.

Figure 2:
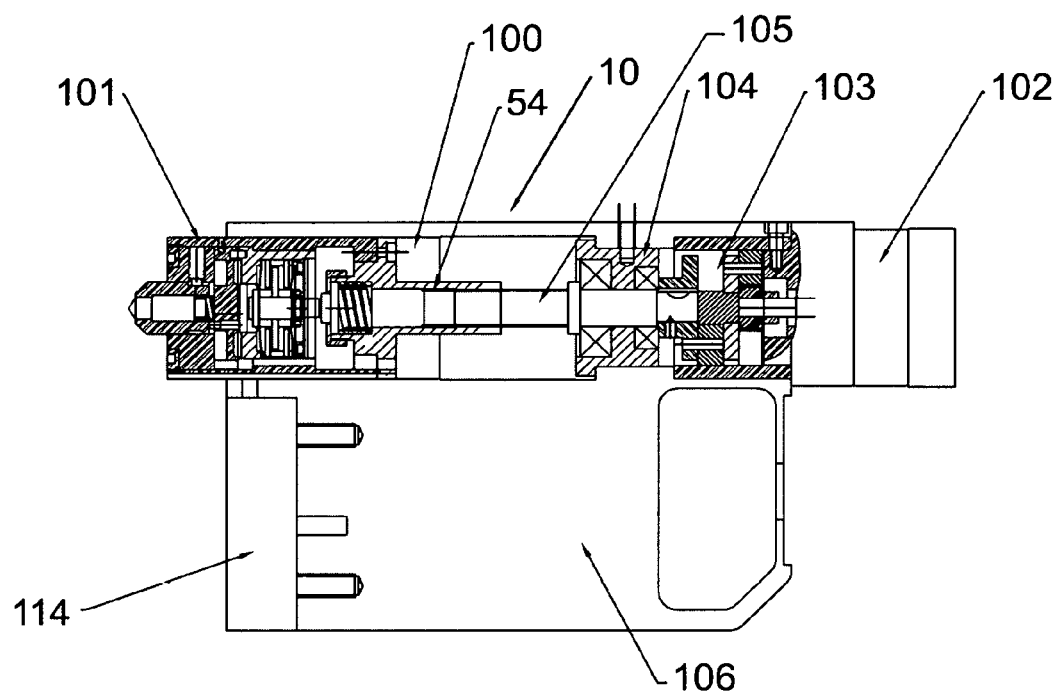
FIG. 2 is a view of the measuring component of the testing machine according to the above preferred embodiment of the present invention.

FIG. 2 describes in detail the inventive testing machine's measuring component 10. The metallic measuring component includes a housing 100 and a locating slot 114. The housing 100 is perpendicular with the locating slot 114. The locating slot 114 is for attaching different frames, which the user selects based on the test specimen. The measuring component 10 includes a housing 100, presshead 101, motor 102, reduction drive 103, bearing mount 104, and lead screw 105. The housing 100 fixes in place the motor 102, reduction drive 103, and bearing mount 104. The motor 102 is connected to the reduction drive 103, which reduces speed and drives the lead screw 105. The nut 54 at the rear of the presshead 101 converts the rotary motion of lead screw 105 into linear motion. The presshead 101 can freely move in the cavity at the front of the housing 100. The reduction drive 103 is a planetary gear. The metallic measuring component includes a circuit housing 106 that encloses the motion control and driver system circuit, data processing system circuit, data display system circuit, and data communication system circuit.

Figure 3:
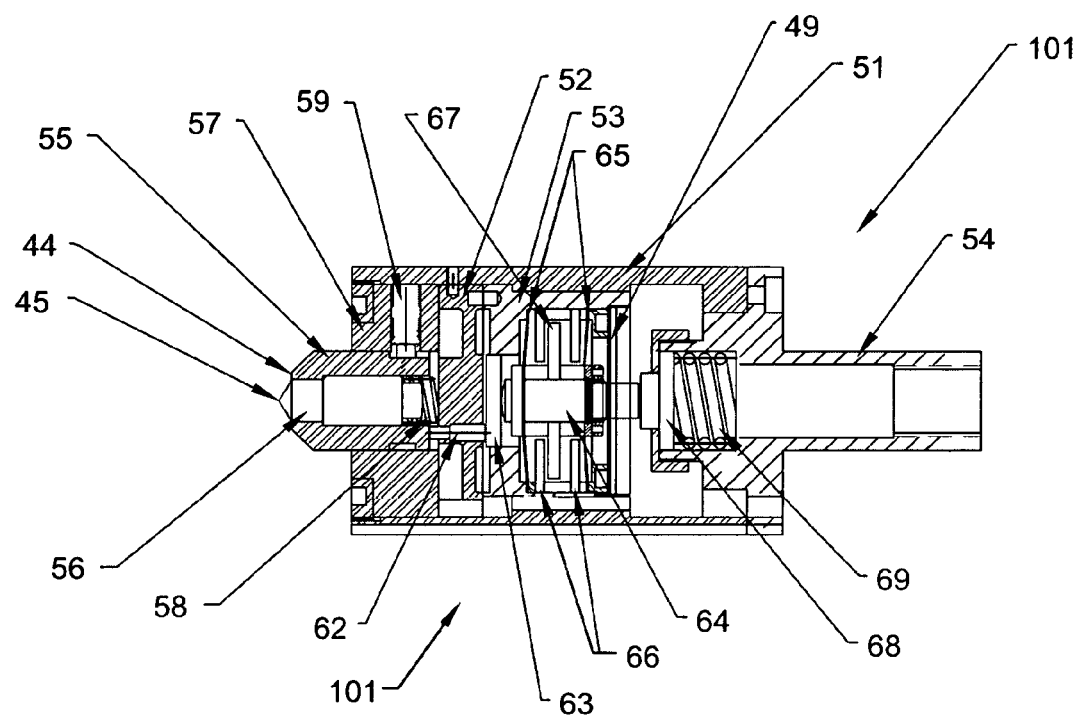
FIG. 3 is a view of the presshead of the measuring component of the testing machine according to the above preferred embodiment of the present invention.

FIG. 3 describes in detail the inventive testing machine's measuring component's 10 presshead 101. The presshead 101 comprises an assembly of components. The assembly includes a presshead housing shell 51, force sensor load cell 52, displacement sensor 53, nut 54, displacement measurement sleeve 55, guide sleeve 57, and indenter 56.

FIG. 3 describes in detail the inventive testing machine's measuring component's 10 presshead assembly. The measuring component's 10 presshead 101 has a presshead housing shell 51. Inside the shell 51 is a cavity coaxially aligned with the indenter 56. Inside the cavity is the guide sleeve 57. Installed on the guide sleeve 57 is a set screw 59. The displacement measurement sleeve 55 is inserted into the guide sleeve's 57 inner hole.

Figure 4:
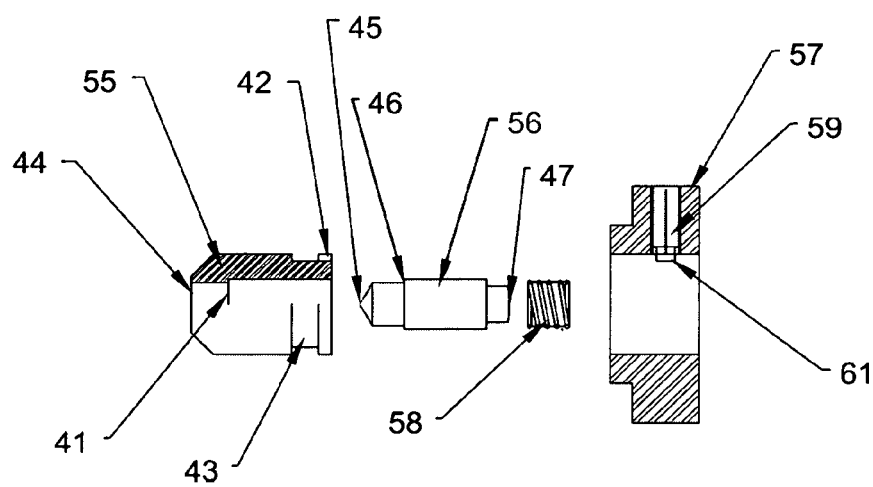
FIG. 4 is a view of the displacement measurement sleeve, the guide sleeve, and the indenter of the presshead of the measuring component of the testing machine according to the above preferred embodiment of the present invention.

FIG. 4 further describes in detail one part of the inventive testing machine's measuring component's 1 presshead assembly. The displacement measurement sleeve 55 has a circumferential groove 43. The displacement measurement sleeve's 55 rear end has a gap 42. This gap 42 meets together with the circumferential groove 43. The guide sleeve 57 set screw tip 61 is positioned barely past the gap 42 into the circumferential groove 43. After rotating a certain angle, the displacement measurement sleeve 55 will lock in place inside the guide sleeve 57. Due to the displacement measurement sleeve's 55 circumferential groove 43 being wider than the set screw tip 61, the displacement measurement sleeve 55 can axially move short distances. The displacement measurement sleeve 55 has an internal cavity, and the indenter 56 is inserted into this cavity. The indenter 56 has a protrusion 46 and the displacement measurement sleeve 55 internal cavity also has a protrusion 41. These protrusions together prevent the indenter 56, when it moves axially inside the displacement measurement sleeve 55, from falling out the displacement measurement sleeve 55. The rear end of the indenter 56 also has a protrusion 47, which is fitted with a spring 58, which during the normal state, causes the indenter front end 45 to protrude out of the displacement measurement sleeve 55.

The indenter front end 45 protrusion is a 120° diamond conical point or very hard alloy ball. The indenter 56 is coaxial with the presshead 101.

FIG. 3 further describes the measuring component's 10 presshead 101 in detail.

Inside the presshead housing shell 51 is a cavity which is concentric with the presshead 101. The cavity contains a force sensor load cell 52. The force sensor load cell 52 is a round-style strain gage transducer. This kind of load cell is well-known technology, and does not warrant further discussion. Situated on the face of the force sensor load cell 52 are three through-holes along a circle, spaced 120° apart. These three through-holes contain within three transmission pins 62, which are used to move axially. One end of each transmission pin 62 contacts the displacement measurement sleeve 55, and the other end contacts the transmission plate 63.

Inside the presshead housing shell 51 is a cavity which is concentric with the presshead 101. The cavity contains a displacement sensor 53 comprising a transmission plate 63, sensor axle 64, and two round steel leaves 65. The round steel leaves' 65 outer edges are fixed inside the displacement sensor's 53 cavity. These two steel leaves' 65 centers are fixed to the sensor axle 64. This structure prevents the sensor axle 64 from moving radially thus restricting the sensor axle 64 to only moving small distances axially. This type of structure ensures the precision of the displacement sensor 53. One end of the sensor axle 64 contacts the transmission plate 63 and the other end contacts the spring pad 68.

The displacement sensor 53 further comprises two fixed electrical terminals 66, fastened inside the internal cavity, and a moveable electrical terminal 67, fixed on the sensor axle 64. When the sensor axle 64 moves axially, the moveable electrical terminal 67 moves along with it, between the two fixed electrical terminals 66. The fixed electrical terminals 66 and the moveable electrical terminal 67 form two capacitances. These two capacitances, between the two fixed electrical terminals 66 and moveable electrical terminal 67, vary as the sensor axle 64 moves, and the difference between the two capacitances is proportional to the axial displacement of the sensor axle 64. The difference between the two capacitances is also proportional to the depth of the indentation on surface of the test specimen 30 caused by the indenter 56.

The displacement sensor 53 further comprises a capacitance conditioning circuit 49 inside the sensor cavity, which converts the capacitance signal into an amplified analog signal.

Another option for the displacement sensor is to use an optical grating sensor. Another substitute for the displacement sensor is a Linear Variable Differential Transformer sensor.

The end of the presshead housing shell 51 is fitted with a nut 54, and the nut 54 is coaxially aligned with the presshead. The nut 54 has a cavity which contains a spring 69 and a spring pad 68. The spring pad 68 has a rear end that contacts the spring 69, and its front end contacts the sensor axle 64. The spring 69 pushes onto the spring pad 68, which in turn pushes onto the sensor axle 64, which in turn pushes onto the transmission plate 63, which in turn pushes onto the transmission pins 62, which in turn pushes onto the displacement measurement sleeve 55. In the absence of measuring, this is the normal state.

FIGS. 5 to 8 are schematics of the measurement device's measurement process which follows ASTM E18 Rockwell Hardness Testing Standard.

Figures 5, 6:
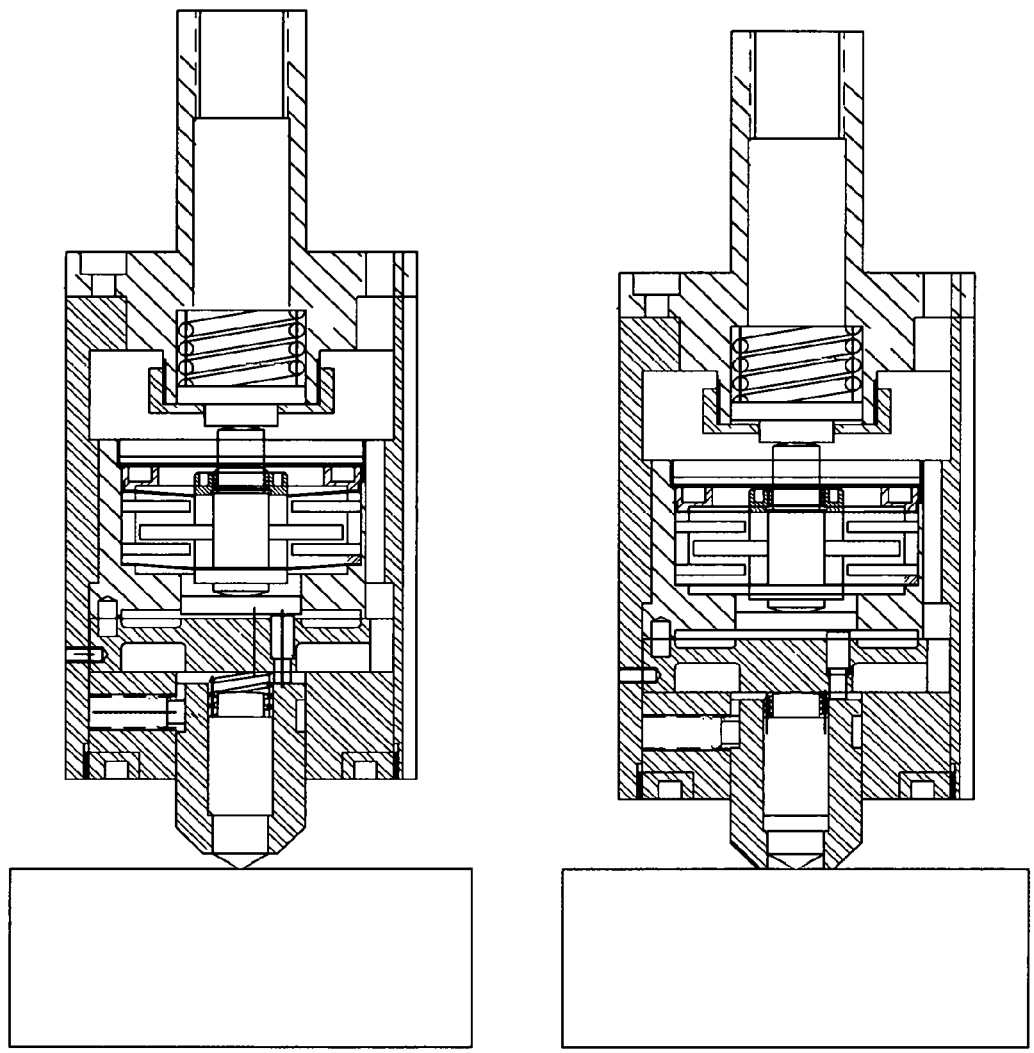
FIGS. 5 to 8 are views of the presshead with indenter applying a force on the test specimen and generating an indentation, following NIST's standard's testing procedure according to the above preferred embodiment of the present invention.

FIG. 5 is a schematic of the measurement component's presshead 101 state before testing. The indenter 56 is being pressed by the spring 58, so the indenter front end 45 is protruding out of the displacement measurement sleeve 55. The rear spring 69 pushes onto the spring pad 68, which in turn pushes onto the sensor axle 64, then to the transmission plate 63, then to the transmission pins 62, and finally to the displacement measurement sleeve 55, which moves out from the guide sleeve 57. The set screw tip 61 prevents the displacement measurement sleeve 55 from falling out.

FIG. 6 is a schematic of the measurement component's pressheads 101 state at the start of the test. The motor 102, spinning in a counterclockwise direction, drives the lead screw 105 through the reduction drive 103, through the nut 54, then moves the presshead 101 forward towards the test specimen 30. The indenter 56, displacement measurement sleeve 55, transmission pins 62, transmission plate 63, sensor axle 64, spring pad 68, and spring 69 moves together along with the presshead 101. Eventually, the indenter front end 45 will contact the test specimen 30 and the indenter 56 cannot move any further. As the presshead 101 continues to move, the displacement measurement sleeve 55 will continue to move along towards the test specimen 30 until the displacement measurement sleeve's 55 front surface 44 aligns with the indenter front end 45. At this point, both the indenter 56 and the displacement measurement sleeve 55 cannot move any further. As the presshead 101 continues to move towards the specimen 30, the transmission pins 62 will contact the immobile displacement measurement sleeve 55, and be stopped from moving further. The transmission pins 62 will in turn stop the transmission plate 63, which will stop the sensor axle 64, which will stop the spring pad 68. The now immobile spring pad 68 causes the spring 69 to compress. The opposing force of the spring 69 clamps the test specimen 30. At this point, the indenter rear end 47 has contacted the force sensor load cell 52.

According to ASTM E18 Standard Test Methods for Rockwell Hardness of Metallic Materials, the inventive testing machine must first apply a preliminary test force F0 on the test specimen.

Figure 7:
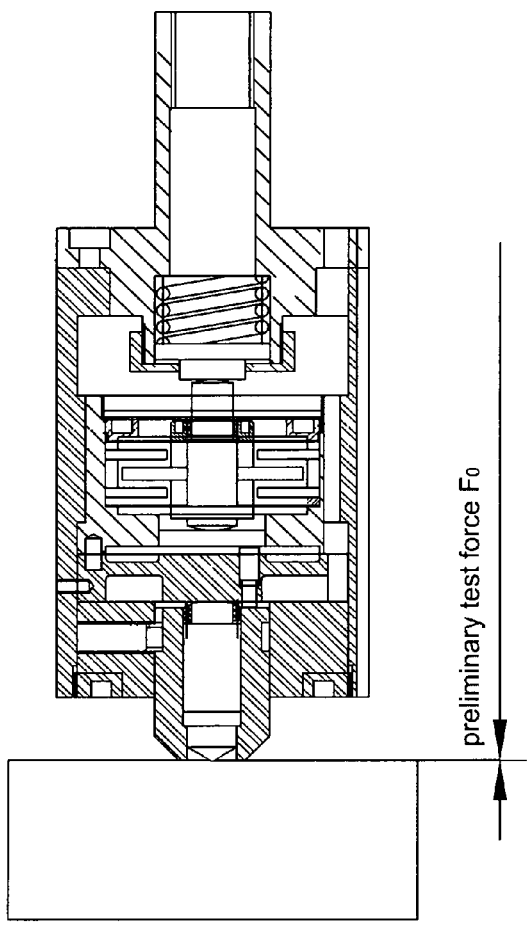

FIG. 7 is a schematic of the measurement component's presshead 101 state during application of a preliminary test force F0 on the test specimen. The motor 102 continues to spin in a counterclockwise direction, applying force to test specimen 30 through the presshead's 101 indenter 56. The indenter rear end 47 applies an equal and opposite force to load cell 52, which measures the force value and feeds it back to the motion control and driver system. The motion control and driver system controls the motor 102, and stops it once the applied force reaches the prescribed value of F0. As dictated by ASTM E18, the inventive testing machine waits for a specified dwell time and then the displacement sensor 53 measures the depth of the indentation on test specimen 30 formed by the indenter 56 after applying F0.

According to ASTM E18 Standard, the inventive testing machine, must then apply an additional test force F1 to achieve a total test force F on the test specimen, where F=F0+F1.

Figure 8:
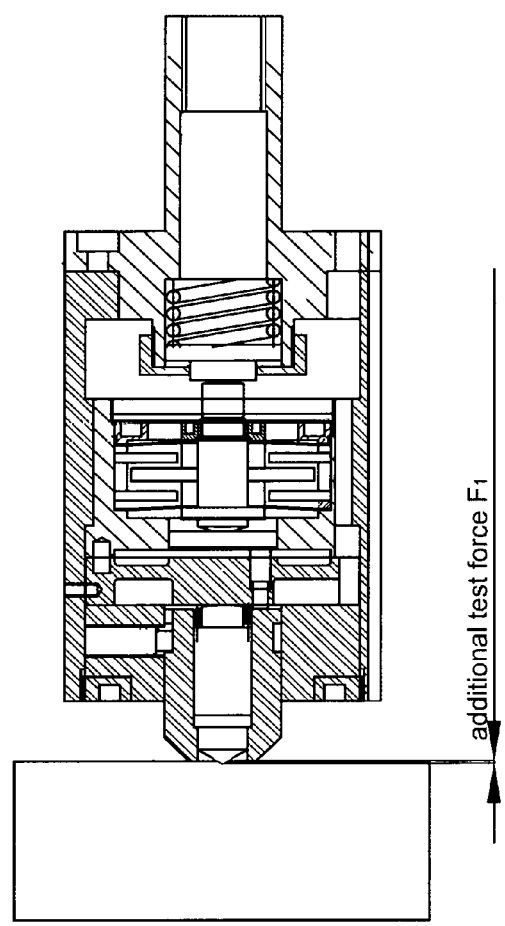

FIG. 8 is a schematic of the measurement component's presshead 101 state during application of the additional test force F1 on the test specimen. The motor 102 starts spinning in a counterclockwise direction again to apply force to test specimen 30 through the presshead's 101 indenter 56. The indenter rear end 47 applies an equal and opposite force to the force sensor load cell 52, which measures the force value and feeds it back to the motion control and driver system. The motion control and driver system controls the motor 102, and stops it once the applied force reaches the prescribed value of F=F0+F1. As dictated by ASTM E18, the inventive testing machine waits for a specified dwell time.

According to ASTM E18 Standard, the additional test force is then to be removed, returning to the preliminary test force F0.

The motor 102 starts spinning in a clockwise direction, drives the lead screw 105 through the reduction drive 103, through the nut 54, and then moves the presshead 101 backwards away from the test specimen 30, reducing the force to test specimen 30 through the presshead's 101 indenter 56. The indenter rear end 47 reduces the force it applies to the force sensor load cell 52, which measures the force value and feeds it back to the motion control and driver system. The motion control and driver system controls the motor 102, and stops it once the applied force reaches the prescribed value of F0. As dictated by ASTM E18, the inventive testing machine waits for a specified dwell time and then the displacement sensor 53 measures the depth of the indentation on test specimen 30, which was formed by the indenter 56 when it applied F=F0+F1.

The data processing system analyzes both indentation depths on the test specimen measured by the displacement sensor, and calculates and outputs the tested hardness. The LCD of the data display system shows the test results. The data communication system transfers the test results to a PC or printer through an USB or Bluetooth™ interface.

The inventive testing machine comprises a module, which comprises a measuring component and a set of different frames. Users select different frames suitable for different test specimens such as long specimens, short specimens, holes or thin-walled tubes.

Figure 9:
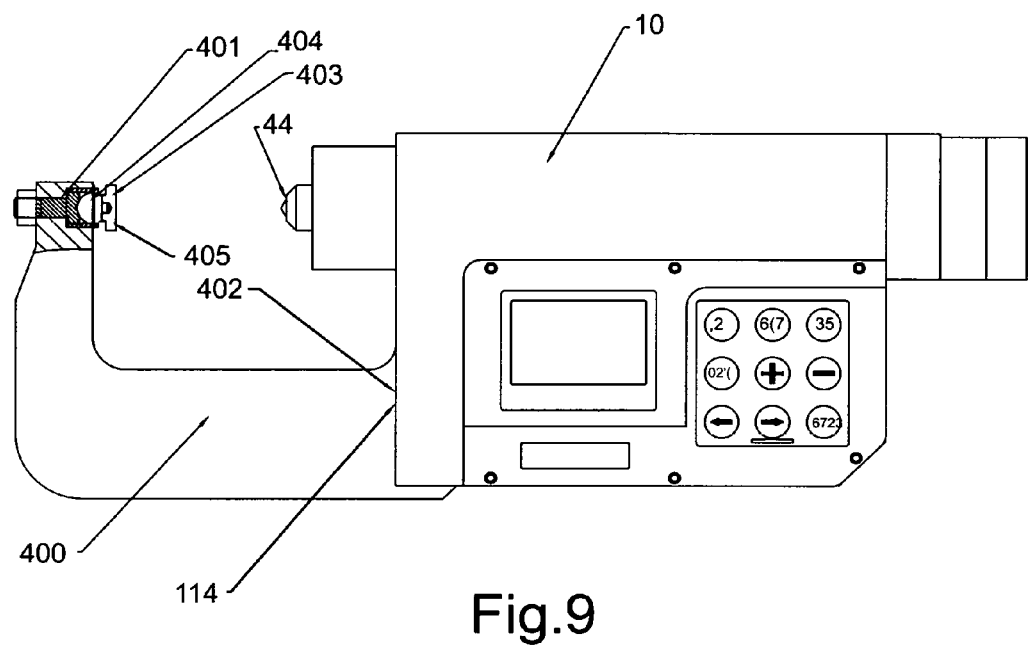
FIG. 9 is a view of the portable testing machine with retaining frame according to the above preferred embodiment of the present invention.

FIG. 9 describes in detail the inventive testing machine's measuring component 10, together with the retaining frame 400 composing a portable hardness tester. The retaining frame 400 has a positioning key 402. The positioning key inserts into the measuring component's 10 locating slot 114. The retaining frame is fastened to the measuring component 10 with a screw. The retaining frame has a cavity 401 which is coaxial with the presshead 101. Inside the cavity 401 is the self-aligning anvil 403. Whether or not the test specimen's 30 test and rear surfaces are in parallel with each other, the self-aligning anvil 403 will ensure the test specimen's 30 front test surface will be in parallel with the displacement measurement sleeve's 55 front surface 44 to ensure high accuracy. Upon contact between the test specimen's 30 front test surface and the displacement measurement sleeve's 55 front surface 44, the self-aligning anvil 403 will move such that the two surfaces are in parallel with one another. The self-aligning anvil 403 comprises a half ball 404 and an anvil 405. The inventive testing machine provides many retaining frames of different sizes to accommodate different sized test specimens.

Figure 10:
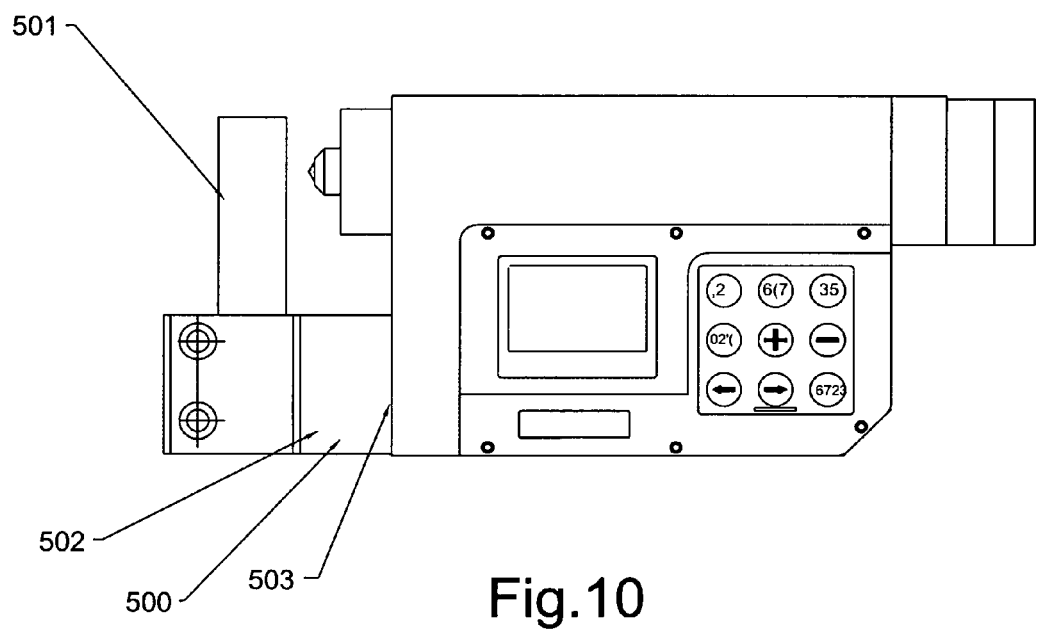
FIG. 10 is a view of the portable testing machine with tube-testing frame according to the above preferred embodiment of the present invention.

FIG. 10 describes in detail the inventive testing machine's measuring component 10 together with the thin-walled tube testing frame 500 composing a portable hardness tester for testing different types of tubes. The thin-walled tube testing frame 500 comprises a cylinder 501 and an L-shaped frame 502. The cylinder 501 fastens to the L-shaped frame 502 with a screw. The thin-walled tube testing frame 500 has a positioning key 503, which inserts into the measuring component's 10 locating slot 114. The thin-walled tube testing frame 500 is fastened to the measuring component 10 with a screw.

Figure 12:
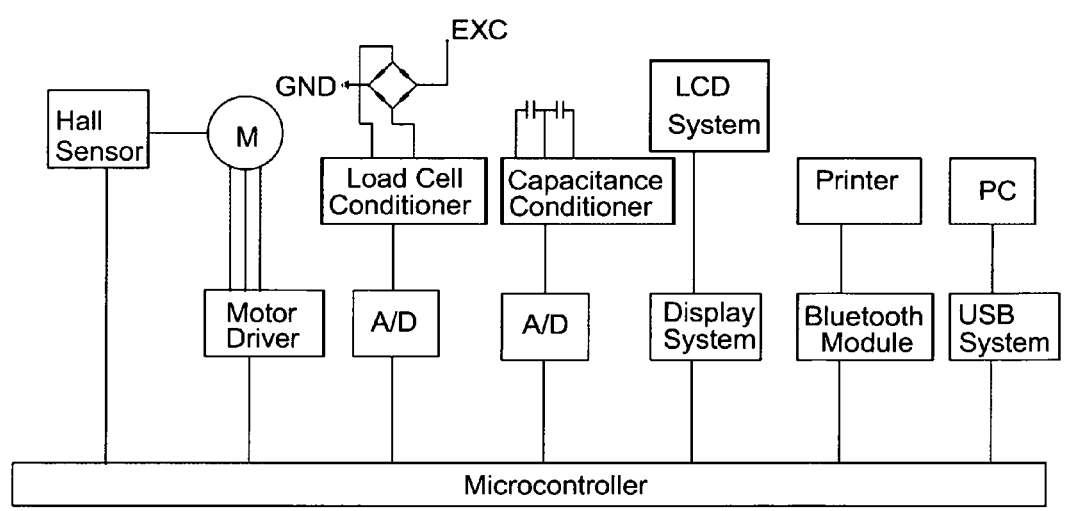
FIG. 12 is an electronic circuit block diagram and schematic diagram of the testing machine according to the above preferred embodiment of the present invention.

FIG. 12 describes the inventive testing machine's measuring component's 10 basic block diagram and does not warrant further discussion.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

The invention claimed is:

1. A modular hardness testing machine comprising:
   a) a measuring component and a set of frames, wherein the measuring component includes a measuring component housing and a locating slot;
   b) the measuring component has the locating slot configured to receive a frame, wherein the locating slot allows a user to modularly interchange the frame;
   c) the measuring component housing encloses a presshead which encloses a load cell having through-holes holding transmission pins, wherein a first end of each transmission pin contacts a displacement measurement sleeve, and wherein a second end contacts a transmission plate;
   d) a motor mounted to the measuring component housing, wherein the motor is connected to a reduction drive; wherein the reduction drives a lead screw mounted on a bearing mount; and
   e) a moveable presshead driven by the lead screw, wherein the measuring component includes a circuit housing for the electronics system, wherein the electronics system comprises: a motion control and driver system; a data processing system; a data display system; and a data communication system, wherein the motion control and driver system is configured as a closed-loop digital control system, which generates force to the indenter, wherein the system driver is configured to move the presshead forward or backward, wherein the data processing system calculates and analyzes the hardness according to indentation on the test specimen produced by the indenter, wherein the LCD of the data display system displays test results, wherein the data communication system transfers test results to a PC or printer.

2. The modular hardness testing machine of claim 1, wherein the housing is mounted perpendicularly to the locating slot, wherein the locating slot is configured to receive the frame, wherein a nut converts the rotary motion of the lead screw into linear motion.

3. The modular hardness testing machine of claim 2, wherein said reduction drive is a planetary gear; wherein the motor is connected to the reduction drive, which reduces speed and drives the lead screw.

4. The modular hardness testing machine of claim 2, wherein the presshead comprises an assembly of components, wherein the assembly includes: a presshead housing; a force sensor; a displacement sensor; a nut; a displacement measurement sleeve; a guide sleeve; and an indenter.

5. The modular hardness testing machine of claim 2, further including an electronic system power supply configured as a rechargeable battery system.

6. The modular hardness testing machine of claim 1, wherein the load cell is a round-style strain gage transducer.

7. The modular hardness testing machine of claim 1, wherein the load cell spaces three through-holes are configured along a circle, spaced 120° apart, wherein the three through-holes contain three transmission pins that move in an axial direction, wherein one end of each transmission pin contacts the displacement measurement sleeve, and the other end of each transmission pin contacts the transmission plate.

8. The modular hardness testing machine of claim 1, wherein further comprising a displacement sensor, wherein the displacement sensor is a capacitive type sensor, optical grating sensor, or linear variable differential transformer sensor, wherein the displacement sensor directly measures the displacement of the indenter at the surface of the specimen.

9. The modular hardness testing machine of claim 1, further comprising a guide sleeve, and a set screw installed on the guide sleeve, wherein the displacement measurement sleeve is inserted into the guide sleeve's inner hole, wherein the displacement measurement sleeve has a circumferential groove, wherein the displacement measurement sleeve has a rear end that has a gap, wherein the gap meets together with the circumferential groove, wherein the guide sleeve's set screw's tip is positioned past the gap into the circumferential groove, wherein the displacement measurement sleeve is configured so that after rotating a certain angle, the displacement measurement sleeve will lock in place inside the guide sleeve wherein the displacement measurement sleeve's circumferential groove is wider than the set screw's tip so that the displacement measurement sleeve can axially move distances.

10. The modular hardness testing machine of claim 9, wherein the displacement measurement sleeve has an internal cavity, and the indenter is inserted into the internal cavity, wherein the front end of the indenter has a protrusion and the displacement measurement sleeve's internal cavity also has a protrusion, wherein the protrusion of the front end of the indenter and the protrusion of the displacement measurement sleeve's internal cavity together prevent the indenter, when it moves axially inside the displacement measurement sleeve, from falling out of the displacement measurement sleeve, wherein the rear end of the indenter also has a protrusion, which is fitted with a spring, which during a normal state causes the indenter's front end to protrude out of the displacement measurement sleeve.

11. The modular hardness testing machine of claim 1, further including a capacitive type displacement sensor which comprises: a transmission plate; a sensor axle; and a pair of round steel leaves, wherein the pair of round steel leaves have outer edges that are fixed inside a displacement sensor cavity, which is a cavity formed on the displacement sensor, wherein the pair of round steel leaves have centers that are fixed to the sensor axle, wherein one end of the sensor axle contacts the transmission plate and the other end contacts a spring pad, whereby the sensor axle is restrained from moving radially thus restricting the sensor axle to only moving distances axially.

12. The modular hardness testing machine of claim 11, wherein the capacitive type displacement sensor further comprises two fixed electrical terminals, fastened inside the internal cavity, and a moveable electrical terminal, fixed on the sensor axle, wherein when the sensor axle moves axially, the moveable terminal moves along with it, between the two fixed terminals, wherein the fixed terminals and the moveable terminal form two capacitances, wherein these two capacitances, between the two fixed terminals and moveable terminal, vary as the sensor axle moves, and the difference between the two capacitances is proportional to the axial displacement of the sensor axle, wherein the difference between the two capacitances is also proportional to the depth of the indentation on surface of the test specimen caused by the indenter.

13. The modular hardness testing machine of claim 11, wherein the capacitive type displacement sensor further comprises a capacitance conditioning circuit inside the sensor cavity, which converts the capacitance signal into an amplified analog signal.

14. The modular hardness testing machine of claim 11, wherein the end of the presshead housing is fitted with a nut, and the nut is coaxially aligned with the presshead, wherein the nut has a cavity which contains a spring and a spring pad, wherein the spring pad's first end contacts the spring, and its second end contacts the sensor axle, wherein the spring pushes onto the spring pad, which in turn pushes onto the sensor axle, which in turn pushes onto the transmission plate, which in turn pushes onto the transmission pins, which in turn pushes onto the displacement measurement sleeve.

15. The modular hardness testing machine of claim 1, further comprising a second set of frames including: a column style stand which forms the testing apparatus, wherein the column style stand comprises a box frame, which is fixed to a fastening fixture, screw, anvil, nut, and base, wherein the fastening fixture connects the measuring component to the stand, wherein the box frame has equally spaced slots, wherein the fastening fixture has a positioning key, which inserts into one of the slots, wherein the fastening fixture can be inserted into any of the slots on the box frame and fastened onto the box frame with a screw, wherein the anvil is used for supporting test specimens, and is attached to the base by the nut, wherein one end of the anvil is a screw, which screws into the nut, wherein the anvil is also used to make small adjustments in the height between the test specimen and indenter, wherein the fastening fixture is configured so that repositioning the fastening fixture on the box frame makes adjustments in the height between the test specimen and indenter, wherein the column style stand can stand in a variety of different positions including a vertical, horizontal and diagonal.

16. The modular hardness testing machine of claim 1, wherein the measuring component together with the retaining frame comprises a portable hardness tester, wherein the retaining frame has a positioning key, wherein the positioning key inserts into the measuring component's locating slot, wherein the retaining frame is fastened to the measuring component with a screw, wherein the retaining frame has a cavity which is coaxial with the presshead, wherein the cavity has a self-aligning anvil.

17. The modular hardness testing machine of claim 1, wherein the measuring component together with the thin-walled tube testing frame composing a portable hardness tester for testing different types of tubes, wherein the thin-walled tube testing frame comprises a cylinder and an L-shaped frame, wherein the cylinder fastens to the L shape frame with a screw, wherein the thin-walled tube testing frame has a positioning key, which inserts into the measuring component's locating slot, wherein the thin-walled tube testing frame is fastened to the measuring component with a screw.

\* \* \* \* \*